United States Patent [19]

Knops et al.

[11] Patent Number: 4,670,044

[45] Date of Patent: Jun. 2, 1987

[54] N-METHYL-4-PYRIDONES

[75] Inventors: Hans-Joachim Knops, Monheim; Peter Babczinski, Wuppertal; Ludwig Eue, Leverkusen; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 760,198

[22] Filed: Jul. 29, 1985

[30] Foreign Application Priority Data

Aug. 17, 1984 [DE] Fed. Rep. of Germany ....... 3430232

[51] Int. Cl.$^4$ .................... C07D 401/04; A01N 43/40
[52] U.S. Cl. ........................................ 71/92; 546/276; 546/278; 546/279
[58] Field of Search ...................... 546/276, 278, 279; 71/92, 94

[56] References Cited

U.S. PATENT DOCUMENTS 4,152,136  5/1979  Taylor ................................ 546/283

FOREIGN PATENT DOCUMENTS 0073999  3/1983  European Pat. Off. .
2537753  3/1976  Fed. Rep. of Germany .

Primary Examiner—Jane T. Fan
Attorney, Agent, or Firm—Sprung Horn Kramer & Woods

[57] ABSTRACT

Novel herbicidally active N-methyl-4-pyridones of the formula

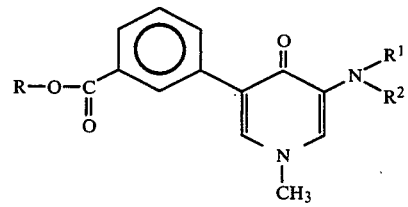

in which
R represents hydrogen, alkyl, alkenyl, alkynyl, alkoxyalkyl, halogenoalkyl, cycloalkyl, optionally substituted aralkyl or one equivalent of an ammonium or metal cation and
$R^1$ and $R^2$, together with the nitrogen atom to which they are bonded, represent an optionally substituted heterocyclic radical.

10 Claims, No Drawings

N-METHYL-4-PYRIDONES

The invention relates to new N-methyl-4-pyridones, several processes for their preparation and their use as herbicides.

It is already known that certain N-substituted 4-pyridones, such as, for example, 1-methyl-3-(1,2,4-triazol-1-yl)-5-(3-trifluoromethylphenyl)-4-pyridone, have herbicidal properties, and in particular also selective herbicidal properties (compare, for example, European Published Application A2-0,073,999 and U.S. Pat. No. 4,451,282).

However, the herbicidal action of these already known compounds against harmful plants, and also their tolerance towards crop plants, is not always completely satisfactory in all fields of application.

New N-methyl-4-pyridones of the general formula (I)

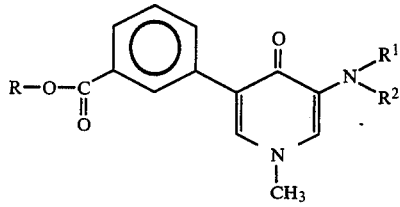

in which

R represents hydrogen, alkyl, alkenyl, alkynyl, alkoxyalkyl, halogenoalkyl, cycloalkyl, optionally substituted aralkyl or one equivalent of an ammonium or metal cation and $R^1$ and $R^2$, together with the nitrogen atom to which they are bonded, represent an optionally substituted heterocyclic radical, have been found.

It has furthermore been found that the new N-methyl-4-pyridones of the general formula (I) are obtained by a process in which (a) trifluoromethylphenyl-pyridones of the formula (II)

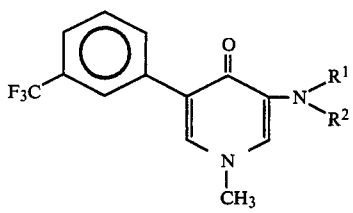

in which $R^1$ and $R^2$ have the abovementioned meaning, are hydrolyzed with concentrated sulphuric acid, or in which (b) the carboxylic acids obtainable by process (a), of the formula (Ia)

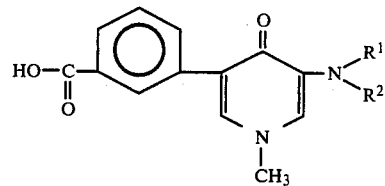

in which $R^1$ and $R^2$ have the abovementioned meaning, are reacted with hydroxy compounds of the formula (III)

$$R'\text{—OH} \quad (III)$$

in which R' represents alkyl, alkenyl, alkynyl, alkoxyalkyl, halogenoalkyl, cycloalkyl, optionally substituted aralkyl or one equivalent of a metal cation or quaternary ammonium ion, or with amines of the formula (IV)

in which $R^3$, $R^4$ and $R^5$ independently of one another in each case represent hydrogen or alkyl, cycloalkyl or aralkyl, if appropriate in the presence of a diluent and if appropriate in the presence of a catalyst, or in which (c) the esters obtainable by process (b), of the formula (Ib),

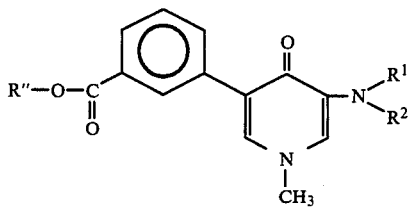

in which

R″ represents lower alkyl and $R^1$ and $R^2$ have the abovementioned meaning, are reacted with alcohols of the formula (IIIa)

$$R'''\text{—OH} \quad (IIIa)$$

in which R‴ represents alkyl, alkenyl, alkynyl, alkoxyalkyl, halogenoalkyl, cycloalkyl or optionally substituted aralkyl, if appropriate in the presence of a diluent and if appropriate in the presence of a catalyst.

Finally, it has been found that the new N-methyl-4-pyridones of the general formula (I) have herbicidal properties, in particular also selective herbicidal properties.

Surprisingly, the N-methyl-4-pyridones of the general formula (I) according to the invention have a considerably better herbicidal activity against harmful plants, with a comparable selectivity towards useful plants, than the N-substituted 4-pyridones which are known from the prior art, such as, for example, 1-methyl-3-(1,2,4-triazol-1-yl)-5-(3-trifluoromethylphenyl)-4-pyridone, which are closely related compounds chemically and from the point of view of their action.

Formula (I) provides a general definition of the N-methyl-4-pyridones according to the invention. Preferred compounds of the formula (I) are those in which R represents hydrogen, or represents alkyl, alkenyl or alkynyl, each of which is straight-chain or branched and has up to 18 carbon atoms, or represents straight-chain or branched alkoxyalkyl with in each case up to 12 carbon atoms in the individual alkyl parts, or represents straight-chain or branched halogenoalkyl with up to 12 carbon atoms and up to 18 identical or different halogen atoms, or represents cycloalkyl with 3 to 7 carbon atoms, or represents straight-chain or branched aralkyl which has up to 4 carbon atoms in the alkyl part and 6 to 10 carbon atoms in the aryl part and is optionally monosubstituted or polysubstituted by identical or different substituents in the aryl part, possible substituents being: halogen, cyano, nitro and alkyl, alkoxy or halogenoalkyl, each of which is straight-chain or branched and has up to 4 carbon atoms and, where appropriate, up to 9 identical or different halogen atoms, or represents one equivalent of an alkali metal or alkaline earth metal cation, or represents an ammonium ion of the formula

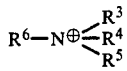

wherein

R$^3$, R$^4$, R$^5$ and R$^6$ independently of one another in each case represent hydrogen, or represent straight-chain or branched alkyl with up to 18 carbon atoms, or represent cycloalkyl with 3 to 7 carbon atoms, or represent straight-chain or branched aralkyl with up to 4 carbon atoms in the alkyl part and 6 to 10 carbon atoms in the aryl part, and R$^1$ and R$^2$, together with the nitrogen atom to which they are bonded, represent a 5-membered heterocyclic radical which as 1 to 3 nitrogen atoms and is optionally substituted by alkyl or alkoxy with in each case up to 4 carbon atoms or halogen.

Particularly preferred compounds of the formula (I) are those in which R represents hydrogen, methyl, ethyl, n- or i- propyl, n-, i-, s- or t-butyl, n- or i-pentyl, n- or i-hexyl, n- or i-heptyl, n- or i-octyl, n- or i-nonyl, n- or i-decyl, n- or i-dodecyl, allyl, butenyl, pentenyl, hexenyl, propargyl, butynyl, pentynyl, hexynyl, methoxymethyl, methoxyethyl, ethoxyethyl, isopropoxyethyl, methoxypropyl, chloromethyl, dichloromethyl, trichloromethyl, trifluoromethyl, 2-chloroethyl, 2,2,2-trichloroethyl, 2-bromoethyl, 2,2,2-tribromoethyl, 3-chloropropyl, cyclopropyl, cyclopentyl, cyclohexyl or cycloheptyl, or represents benzyl or phenethyl, each of which is optionally mono-, di- or tri-substituted by identical or different substituents from the group comprising fluorine, chlorine, bromine, methyl, ethyl, methoxy, ethoxy, cyano and trifluoromethyl, or represents one equivalent of a sodium, potassium, calcium, magnesium or barium ion or ammonium ion of the formula

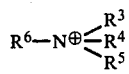

wherein

R$^3$, R$^4$, R$^5$ and R$^6$ independently of one another each represent hydrogen, methyl, ethyl, n- or i- propyl, n-, i-, s- or t-butyl, n- or i-pentyl, n- or i-hexyl, n- or i-heptyl, n- or i-octyl, cyclopentyl, cyclohexyl or benzyl and R$^1$ and R$^2$, together with the nitrogen atom to which they are bonded, represent the following heterocyclic radicals, each of which is optionally substituted by methyl, methoxy and/or chlorine: 1,2,4-triazol-1-yl, imidazol-1-yl and pyrazol-1-yl.

The following N-methyl-4-pyridones of the general formula (I) may be mentioned specifically, in addition to the compounds mentioned in the preparation examples:

TABLE 1

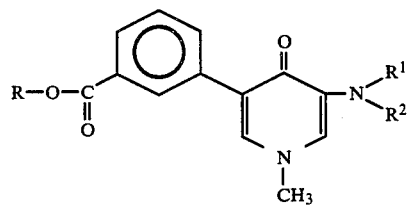

| R | $-N\begin{smallmatrix}R^1\\R^2\end{smallmatrix}$ | R | $-N\begin{smallmatrix}R^1\\R^2\end{smallmatrix}$ |
|---|---|---|---|
| H | —N⟨N=N⟩ | CH$_3$(CH$_2$)$_3$—CH(CH$_3$)—CH$_2$— | —N⟨N=N⟩ |
| CH$_3$ | —N⟨N=N⟩ | (CH$_3$)$_2$CH—CH$_2$—CH(CH$_3$)— | —N⟨N=N⟩ |
| C$_2$H$_5$ | —N⟨N=N⟩ | (CH$_3$)$_3$C— | —N⟨N=N⟩ |

TABLE 1-continued

Structure (I): 3-(substituted)-phenyl ester substituted with R-O-C(=O)- on phenyl ring, attached to 4-oxo-1-methyl-1,4-dihydropyridine bearing -N(R¹)(R²) group.

| R | -N(R¹)(R²) | R | -N(R¹)(R²) |
|---|---|---|---|
| n-C$_3$H$_7$ | 1,2,4-triazol-1-yl | Cl—CH$_2$CH$_2$— | 1,2,4-triazol-1-yl |
| i-C$_3$H$_7$ | 1,2,4-triazol-1-yl | | |
| t-C$_4$H$_9$ | 1,2,4-triazol-1-yl | C$_6$H$_5$—CH$_2$— | 1,2,4-triazol-1-yl |
| (CH$_3$)$_2$CH—CH$_2$CH$_2$— | 1,2,4-triazol-1-yl | cyclohexyl | 1,2,4-triazol-1-yl |
| (C$_2$H$_5$)$_2$CH—CH$_2$— | 1,2,4-triazol-1-yl | Na$^\oplus$ | 1,2,4-triazol-1-yl |
| CH$_3$—(CH$_2$)$_5$— | 1,2,4-triazol-1-yl | K$^\oplus$ | 1,2,4-triazol-1-yl |
| CH$_3$(CH$_2$)$_3$CH(C$_2$H$_5$)—CH$_2$— | 1,2,4-triazol-1-yl | NH$_4^\oplus$ | 1,2,4-triazol-1-yl |
| H$_2\overset{\oplus}{N}$(i-C$_3$H$_7$)$_2$ | 1,2,4-triazol-1-yl | n-C$_4$H$_9$ | imidazol-1-yl |
| (cyclohexyl)$_2$NH$_4^\oplus$ | 1,2,4-triazol-1-yl | i-C$_4$H$_9$ | imidazol-1-yl |
| C$_6$H$_5$—CH$_2$—$\overset{\oplus}{N}$(CH$_3$)$_3$ | 1,2,4-triazol-1-yl | s-C$_4$H$_9$— | imidazol-1-yl |

TABLE 1-continued (I)

| R | $-N\begin{smallmatrix}R^1\\R^2\end{smallmatrix}$ | R | $-N\begin{smallmatrix}R^1\\R^2\end{smallmatrix}$ |
|---|---|---|---|
| $(C_2H_5)_3\overset{\oplus}{N}H$ | 1,2,4-triazol-1-yl | t-$C_4H_9$ | 1,2,4-triazol-1-yl |
| n-$C_4H_9$ | 1,2,4-triazol-1-yl | $CH_3OCH_2CH_2-$ | 1,2,4-triazol-1-yl |
| i-$C_4H_9$ | 1,2,4-triazol-1-yl | $CH_2=CH-CH_2-$ | 1,2,4-triazol-1-yl |
| s-$C_4H_9$ | 1,2,4-triazol-1-yl | $HC\equiv C-CH_2-$ | 1,2,4-triazol-1-yl |
| n-$C_3H_7-\overset{\oplus}{N}H_3$ | 1,2,4-triazol-1-yl | n-$C_6H_{13}$ | imidazol-1-yl |
| $H_2\overset{\oplus}{N}(i-C_4H_9)_2$ | 1,2,4-triazol-1-yl | $Cl-CH_2CH_2-$ | imidazol-1-yl |
| $(n-C_3H_7)_2\overset{\oplus}{N}H_2$ | 1,2,4-triazol-1-yl | $CH_3O-CH_2CH_2-$ | imidazol-1-yl |
| $(CH_3)_2\overset{\oplus}{N}H_2$ | 1,2,4-triazol-1-yl | $CH_2=CH-CH_2-$ | imidazol-1-yl |
| $(C_2H_5)_2\overset{\oplus}{N}H_2$ | 1,2,4-triazol-1-yl | $HC\equiv C-CH_2-$ | imidazol-1-yl |
| $(n-C_4H_9)_2\overset{\oplus}{N}H_2$ | 1,2,4-triazol-1-yl | $C_6H_5-CH_2-$ | imidazol-1-yl |

TABLE 1-continued
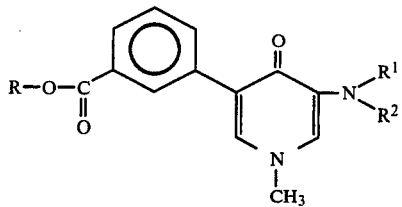
| R | —N(R¹)(R²) | R | —N(R¹)(R²) |
|---|---|---|---|
| [CH₃(CH₂)₃—CH(C₂H₅)—CH₂—]₂N⁺H₂ | 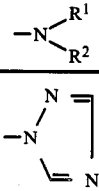 | cyclohexyl | 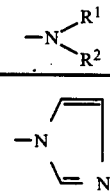 |
| H | 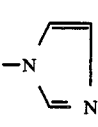 | Na⊕ | 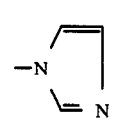 |
| CH₃ |  | K⊕ |  |
| C₂H₅ | 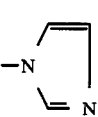 | NH₄⊕ | 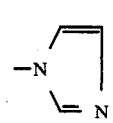 |
| n-C₃H₇ | 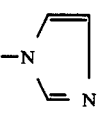 | (C₂H₅)₃N⁺H | 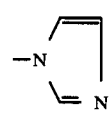 |
| i-C₃H₇ | 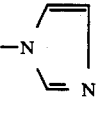 | (i-C₃H₇)₂N⁺H₂ | 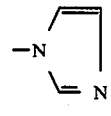 |
| (CH₃)₂N⁺H₂ | 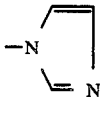 | s-C₄H₉ | 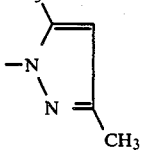 |
| H | 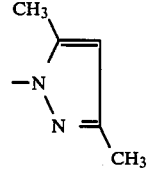 | t-C₄H₉ | 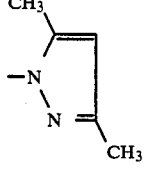 |
| CH₃ | 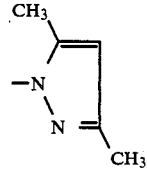 | (CH₃)₂CHCH₂CH₂— | 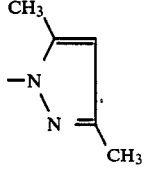 |

TABLE 1-continued (I)

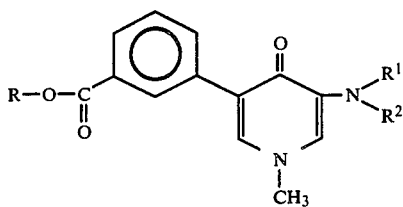

| R | -N(R¹)(R²) | R | -N(R¹)(R²) |
|---|---|---|---|
| $C_2H_5$ | 5-methyl-3-methyl pyrazolyl | $(C_2H_5)_2CHCH_2-$ | 5-methyl-3-methyl pyrazolyl |
| $n\text{-}C_3H_7$ | 5-methyl-3-methyl pyrazolyl | $CH_3-(CH_2)_5-$ | 5-methyl-3-methyl pyrazolyl |
| $i\text{-}C_3H_7$ | 5-methyl-3-methyl pyrazolyl | $CH_3(CH_2)_3CH(C_2H_5)-CH_2-$ | 5-methyl-3-methyl pyrazolyl |
| $n\text{-}C_4H_9$ | 5-methyl-3-methyl pyrazolyl | $CH_3(CH_2)_3CH(CH_3)CH_2-$ | 5-methyl-3-methyl pyrazolyl |
| $i\text{-}C_4H_9$ | 5-methyl-3-methyl pyrazolyl | $(CH_3)_2CH-CH(CH_3)-$ | 5-methyl-3-methyl pyrazolyl |
| $(CH_3)_3C-$ | 5-methyl-3-methyl pyrazolyl | $K^\oplus$ | 5-methyl-3-methyl pyrazolyl |
| $Cl-CH_2CH_2-$ | 5-methyl-3-methyl pyrazolyl | $NH_4^\oplus$ | 5-methyl-3-methyl pyrazolyl |

TABLE 1-continued

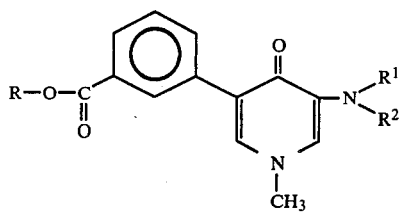
(I)

| R | —N(R¹)(R²) | R | —N(R¹)(R²) |
|---|---|---|---|
| (CH₃)₂NH₂⁺ | 3-methyl-pyrazol-1-yl | H₂N(i-C₃H₇)₂⁺ | 3-methyl-pyrazol-1-yl |
| CH₃OCH₂CH₂— | 3-methyl-pyrazol-1-yl | (C₆H₁₁)₂NH₂⁺ | 3-methyl-pyrazol-1-yl |
| CH₂=CH—CH₂— | 3-methyl-pyrazol-1-yl | C₆H₅CH₂N(CH₃)₃⁺ | 3-methyl-pyrazol-1-yl |
| H—C≡C—CH₂— | 3-methyl-pyrazol-1-yl | (C₂H₅)₃NH⁺ | 3-methyl-pyrazol-1-yl |
| C₆H₅CH₂— | 3-methyl-pyrazol-1-yl | n-C₃H₇—NH₃⁺ | 3-methyl-pyrazol-1-yl |
| C₆H₁₁— | 3-methyl-pyrazol-1-yl | H₂N(i-C₄H₉)₂⁺ | 3-methyl-pyrazol-1-yl |
| Na⁺ | 3-methyl-pyrazol-1-yl | (n-C₃H₇)₂NH₂⁺ | 3-methyl-pyrazol-1-yl |

TABLE 1-continued
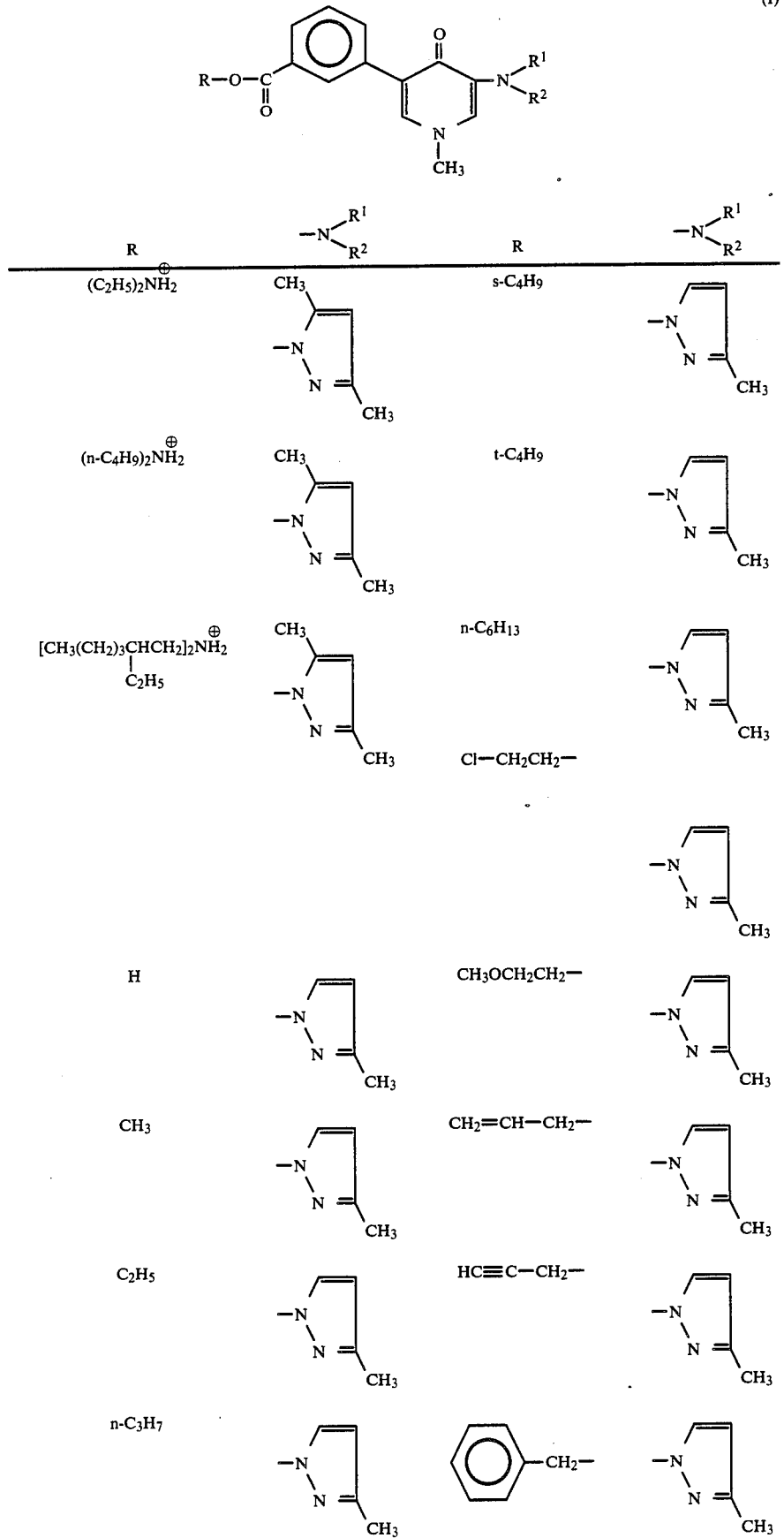

TABLE 1-continued (I)

| R | -N(R¹)(R²) | R | -N(R¹)(R²) |
|---|---|---|---|
| i-C₃H₇ | 3-methyl-pyrazol-1-yl | cyclohexyl | 3-methyl-pyrazol-1-yl |
| n-C₄H₉ | 3-methyl-pyrazol-1-yl | Na⊕ | 3-methyl-pyrazol-1-yl |
| i-C₄H₉ | 3-methyl-pyrazol-1-yl | K⊕ | 3-methyl-pyrazol-1-yl |
| NH₄⊕ | 3-methyl-pyrazol-1-yl | $(C_2H_5)_3\overset{\oplus}{N}H$ | 3-methyl-pyrazol-1-yl |
| $(i\text{-}C_3H_7)_2\overset{\oplus}{N}H_2$ | 3-methyl-pyrazol-1-yl | $(CH_3)_2\overset{\oplus}{N}H_2$ | 3-methyl-pyrazol-1-yl |

If, for example, 1-methyl-3-(pyrazol-1-yl)-5-(3-trifluoromethylphenyl)-4-pyridone and concentrated sulphuric acid are used as starting substances, the course of the reaction in process (a) according to the invention can be represented by the following equation:

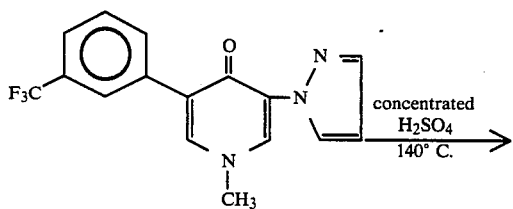

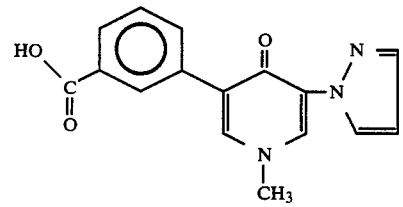

If, for example, 5-(3-carboxyphenyl)-1-methyl-3-(pryazol-1-yl)-4-pyridone and methanol are used as starting substances and thionyl chloride is used as the catalyst, the course of the reaction in process (b) according to the invention can be represented by the following equation:

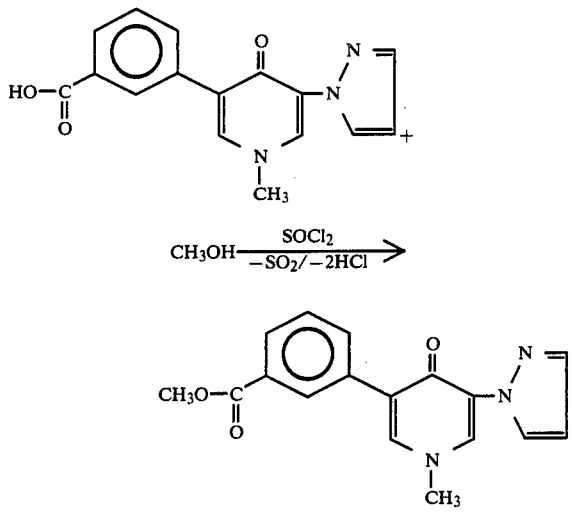

If, for example, 5-(3-methoxycarbonylphenyl)-1-methyl-3-(pyrazol-1yl)-4-pyridone and n-hexanol are used as starting substances and titanium tetraethylate is used as the catalyst, the course of the reaction in process (c) according to the invention can be represented by the following equation:

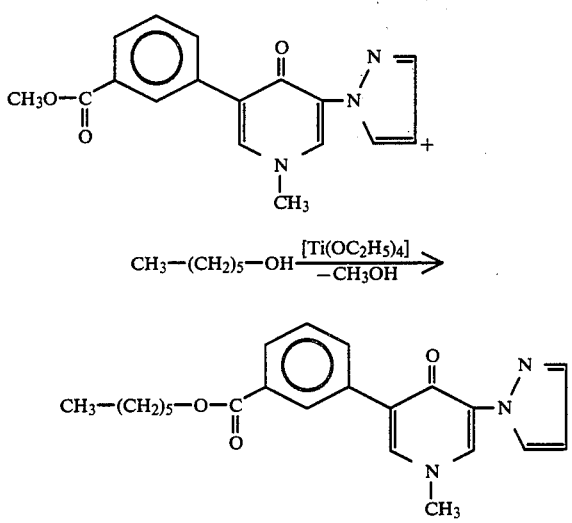

Formula (II) provides a general definition of the trifluoromethylphenylpyridones required as starting substances for carrying out process (a) according to the invention. In this formula (II), $R^1$ and $R^2$ preferably represent those substituents which have already been mentioned as preferred for these substituents in connection with the description of the substances of the formula (I) according to the invention.

The trifluoromethylphenyl-pyridones of the formula (II) are known (compare, for example, European Published Application A2-0,073,999 and U.S. Pat. No. 4,451,282).

Formula (Ia) provides a general definition of the carboxylic acids required as starting substances for carrying out process (b) according to the invention. In this formula (Ia), $R^1$ and $R^2$ likewise preferably represent those radicals which have already been mentioned as preferred for these substituents in connection with the description of the substances of the formula (I) according to the invention.

The carboxylic acids of the formula (Ia) are compounds according to the invention and can be obtained with the aid of process (a) according to the invention.

Formula (III) provides a general definition of the hydroxy compounds furthermore required as starting substances for carrying out process (b) according to the invention. In this formula (III), R' preferably represents alkyl, alkenyl or alkinyl, each of which is straight-chain or branched and has up to 18 carbon atoms, or represents straight-chain or branched alkoxyalkyl with in each case up to 12 carbon atoms in the individual alkyl parts, or represents straight-chain or branched halogenoalkyl with up to 12 carbon atoms and up to 18 identical or different halogen atoms, or represents cycloalkyl with 3 to 7 carbon atoms, or represents straight-chain or branched aralkyl which has up to 4 carbon atoms in the alkyl part and 6 to 10 carbon atoms in the aryl part and is optionally monosubstituted or polysubstituted by identical or different substituents in the aryl part, possible substituents being: halogen, cyano, nitro and alkyl, alkoxy or halogenoalkyl, each of which is straight-chain or branched and has up to 4 carbon atoms and, where appropriate, up to 9 identical or different halogen atoms, or represents one equivalent of an alkali metal or alkaline earth metal cation, or represents a quaternary ammonium ion of the formula

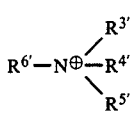

wherein $R^{3'}$, $R^{4'}$, $R^{5'}$ and $R^{6'}$ independently of one another each represent straight-chain or branched alkyl with up to 18 carbon atoms, or represent cycloalkyl with 3 to 7 carbon atoms, or represent straight-chain or branched aralkyl with up to 4 carbon atoms in the alkyl part and 6 to 10 carbon atoms in the aryl part.

The hydroxy compounds of the formula (III) are generally known compounds of organic chemistry.

Formula (IV) provides a general definition of the amines alternatively required as starting substances for carrying out process (b) according to the invention. In this formula (IV), $R^3$, $R^4$ and $R^5$ preferably independently of one another each represent hydrogen, or represent straight-chain or branched alkyl with up to 18 carbon atoms, or represent cycloalkyl with 3 to 7 carbon atoms, or represent straight-chain or branched aralkyl with up to 4 carbon atoms in the alkyl part and 6 to 10 carbon atoms in the aryl part.

The amines of the formula (IV) are likewise generally known compounds of organic chemistry.

Formula (Ib) provides a general definition of the esters required as starting substances for carrying out process (c) according to the invention. In this formula (Ib), $R^1$ and $R^2$ likewise preferably represent those radicals which have already been mentioned as preferred for these substituents in the description of the substances of the formula (I) according to the invention. R" preferably represents methyl, ethyl or n- or i-propyl.

The esters of the formula (Ib) are substances according to the invention and are obtainable with the aid of process (b) according to the invention.

Formula (IIIa) provides a general definition of the alcohols furthermore required as starting substances for carrying out process (c) according to the invention. In this formula (IIIa), R'" preferably represents alkyl, alkenyl or alkinyl, each of which is straight-chain or branched and has 4 to 18 carbon atoms, or represents straight-chain or branched alkoxyalkyl with in each case up to 12 carbon atoms in the individual alkyl parts, or represents straight-chain or branched halogenoalkyl with up to 12 carbon atoms and up to 18 identical or different halogen atoms, or represents cycloalkyl with 3 to 7 carbon atoms, or represents straight-chain or branched aralkyl which has up to 4 carbon atoms in the alkyl part and 6 to 10 carbon atoms in the aryl part and is optionally monosubstituted or polysubstituted by identical or different substituents in the aryl part, possible substituents being: halogen, cyano, nitro and alkyl, alkoxy and halogenoalkyl, each of which is straight-chain or branched and has up to 4 carbon atoms and, where appropriate, up to 9 identical or different halogen atoms.

The alcohols of the formula (IIIa) are likewise generally known compounds of organic chemistry.

Process (a) according to the invention is preferably carried out without a diluent, in bulk.

The reaction temperatures can be varied within a substantial range in carrying out process (a) according to the invention. In general, the reaction is carried out at temperatures between 20° C. and 200° C., preferably at temperatures between 50° C. and 150° C.

For carrying out process (a) according to the invention, in general 1.0 to 15.0 moles, preferably 1.0 to 10.0 moles, of concentrated sulphuric acid are employed per mole of trifluoromethylphenyl-pyridone of the formula (II).

The reaction mixture is stirred at the required temperature until the evolution of gas has ended, diluted with water and then heated under reflux for some hours.

To remove adhering sulphuric acid, the precipitate obtained from the cooled reaction mixture by filtration is neutralised in aqueous-alcoholic solution with barium hydroxide and, after the barium sulphate precipitated has been filtered off, the product is reprecipitated with carbonic acid, filtered off with suction and dried.

Possible diluents for carrying out process (b) according to the invention are organic solvents.

Alcohols, such as methanol, ethanol or n- or isopropanol, are preferably used.

If appropriate (in the case of the esterification reaction), process (b) according to the invention is carried out in the presence of a catalyst. Possible catalysts are all those usually employed for esterification reactions. These include, for example, proton acids, such as, for example, sulphuric acid or p-toluenesulphonic acid, Lewis acids, such as, for example, boron trifluoride, or agents which form acid halides, such as phosphorus pentachloride, phosphorus tribromide or thionyl chloride.

The reaction temperatures can likewise be varied within a substantial range in carrying out process (b) according to the invention. In general, the reaction is carried out at temperatures between 0° C. and +150° C., preferably at temperatures between +20° C. and +100° C.

For carrying out process (b) according to the invention, in general 1.0 to 30.0 moles, preferably 1.0 to 20.0 moles, of hydroxy compound of the formula (III) and, if appropriate, 0.01 to 2.0 moles, preferably 0.1 to 1.0 mole, of catalyst are employed per mole of carboxylic acid of the formula (Ia). The reaction is carried out and the N-methyl-4-pyridones of the formula (I) are worked up and isolated by known and customary processes.

Possible diluents for carrying out process (c) according to the invention are inert organic solvents. Ethers, such as, for example, tetrahydrofuran or dioxane, are preferably used. However, it is also possible for the alcohol of the formula (IIIa) employed as a reaction partner to be used in a corresponding excess as the diluent.

Possible catalysts for process (c) according to the invention are, in particular, acid or basic catalysts. Catalysts which are particularly advantageously used are Lewis acids, such as, for example, boron trifluoride or titanium tetraethylate, or alcoholates with sodium or potassium as the counter-ion of the corresponding alcohol of the formula (IIIa) used for the transesterification. It is also possible to use inorganic zeolites which bond the low molecular weight alcohol liberated and thus remove it from the reaction equilibrium.

The reaction temperatures can likewise be varied within a substantial range in carrying out process (c) according to the invention. In general, the reaction is carried out at temperatures between 0° C. and +120° C., preferably at temperatures between +30° C. and +100° C.

For carrying out process (c) according to the invention, in general 1.0 to 30 moles, preferably 1.0 to 20.0 moles, of alcohol of the formula (IIIa) and 0.01 to 2.0 moles, preferably 0.1 to 1.0 mole, of catalyst are employed per mole of ester of the formula (Ib). The reaction is carried out and the reaction products are worked up and isolated by generally customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed with particularly good success for selectively combating gramineous and broad-leaved weeds in important crop plants, such as, for example, cotton.

The active compounds can be converted to the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in known manner, for example by mixing the active compounds with extenders, that is solvents and/or solid carriers, if appropriate with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4(1H,3H)-dione or N-(2-benzothiazolyl)-N,N'-dimethyl-urea, for combating weeds in cereals; 4-amino-3-methyl-6-phenyl-1,2,4-triazin-5(4H)-one for combating weeds in sugar beet and 4-amino-6-(1,1-dimethylethyl)-3-methylthio-1,2,4-triazin-5(4H)-one for combating weeds in soy beans. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

When applied in appropriate amounts, the active compounds according to the invention moreover also have a fungicidal activity and can be used, for example, for combating rice diseases, such as, for example, against the rice spot disease causative organism (*Pyricularia oryzae*).

The preparation and use of the active compounds according to the invention can be seen from the following examples.

PREPARATION EXAMPLES

Example 1

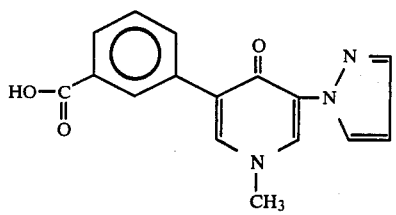

Process a 200 ml (3.74 moles) of concentrated sulphuric acid are added dropwise to 150 g (0.47 mole) of 1-methyl-3-(pyrazol-1-yl)-5-(3-trifluoromethylphenyl)-4-pyridone, with stirring, whereupon the temperature rises to 80° C. to 90° C. When the addition has ended, the mixture is warmed at 140° C., with stirring, until the evolution of gas has ended (about 45 minutes) and is then left to cool to about 40° C. to 50° C., 200 ml of water are carefully added in small portions and, when the addition has ended, the mixture is heated at the reflux temperature for about 60 minutes. The precipitate which separates out of the cooled reaction mixture is filtered off with suction, washed with a little water and dried at 80° C. 148 g (about 80% of theory) of a solid [5-(3-carboxyphenyl)-1-methyl-3-(pyrazol-1-yl)-4-pyridone-sulphuric acid adduct (xn $H_2SO_4$)] are obtained, 40 g of which (about 0.1 mole) are dissolved in a mixture of 700 ml of water and 700 ml of ethanol at 70° C. An aqueous barium hydroxide solution is added dropwise to this solution until the pH reaches 7.5, and the barium sulphate precipitated off with suction over kieselguhr. Solid carbon dioxide is added to the filtrate at room temperature until, at a pH value of 5.5, the free acid precipitates, which is filtered off with suction, washed with a little cold water and dried. 11.5 g (37% of theory) of 5-(3-carboxyphenyl)-1-methyl-3-(pyrazol-1-yl)-4-pyridone of melting point 280° C. are obtained.

EXAMPLE 2

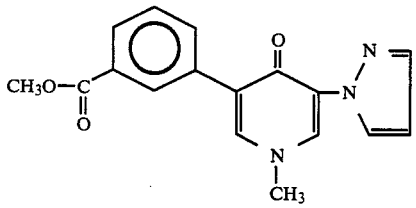

Process b 24 ml (0.33 mole) of thionyl chloride are added dropwise to 30 g (0.09 mole) of 5-(3-carboxyphenyl)-1-methyl-3-(pyrazol-1-yl)-4-pyridone-sulphuric acid adduct in 100 ml of methanol at 0° C. to 10° C.; when the addition has ended, the mixture is stirred at room temperature for 12 hours and concentrated in vacuo, the oil which remains is taken up in 100 ml of water and the mixture is rendered weakly alkaline with aqueous sodium carbonate solution and extracted three times with 100 ml of methylene chloride each time. The combined organic phases are washed with water, dried over sodium sulphate and concentrated in vacuo. The crystals which remain are digested with ether, filtered off with suction and dried. 20 g (91% of theory) of 5-(3-methoxycarbonylphenyl)-1-methyl-3-(pyrazol-1-yl)-4-pyridone of melting point 144° C. are obtained.

EXAMPLE 3

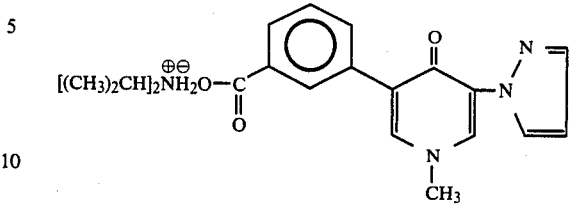

Process b 3 g (0.01 mole) of 5-(3-carboxyphenyl)-1-methyl-3-(pyrazol-1-yl)-4-pyridone and 1.425 ml (0.01 mole) of diisopropylamine in 50 ml of ethanol are stirred at room temperature for one hour and then evaporated to dryness. 2 g (50% of theory) of the diisopropylammonium salt of 3-[1-methyl-5-(pyrazol-1-yl)-4-pyridon-3-yl]-benzoic acid of melting point 174°–175° C. are obtained.

EXAMPLE 4

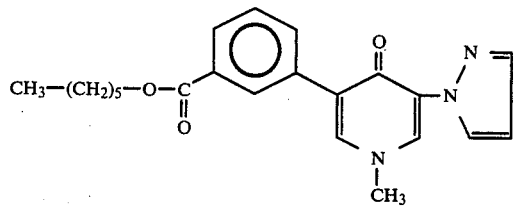

Process c 5 g (0.016 mole) of 5-(3-methoxycarbonylphenyl)-1-methyl-3-(pyrazol-1-yl)-4-pyridone and 16.32 g (0.16 mole) of n-hexanol are extracted under reflux together with 3.64 g (0.016 mole) of titanium tetraethylate in 50 ml of absolute tetrahydrofuran for 12 hours over a Soxhlet extractor filled with 4 Å zeolite. The reaction mixture is concentrated to dryness, the residue is taken up in water and the mixture is extracted three times with methylene chloride; the combined organic phases are dried over sodium sulphate and concentrated in vacuo. The oil which remains is purified chromatographically over a silica gel column (eluant: cyclohexane/ethyl acetate 1:1) and the product is crystallized from ether. 1.3 g (21.4% of theory) of 5-(3-n-hexyloxycarbonylphenyl)-1-methyl-3-(pyrazol-1-yl)-4-pyridone of melting point 96°–97° C. are obtained.

EXAMPLE 5

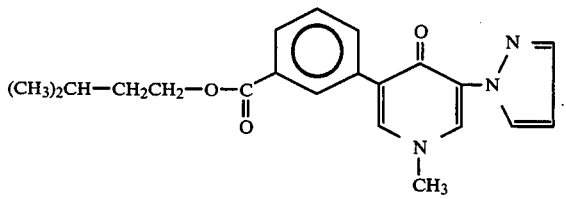

Process c 5 g (0.016 mole) of 5-(3-methoxycarbonylphenyl)-1-methyl-3-(pyrazol-1-yl)-4-pyridone are added to a solution of 0.4 g (0.016 mole) of sodium in 100 ml of 3-methyl-1-butanol, the mixture is heated under reflux for 12 hours and then concentrated to dryness, the residue is taken up in water and the mixture is extracted several times with methylene chloride. The combined organic phases are dried over sodium sulphate and freed from the solvent in vacuo. The oil which remains is chromatographed over a silica gel column (eluant: cyclohexane/ethyl acetate 1:1) and the product is then crystallized from ether.

1.2 g (22% of theory) of 5-[3-(3-methylbutoxycarbonyl)-phenyl]-1-methyl-3-(pyrazol-1-yl)-4-pyridone of melting point 115°–118° C. are obtained.

The following N-methyl-4-pyridones of the general formula (I) are obtained in a corresponding manner in accordance with the general preparation statements:

TABLE 2

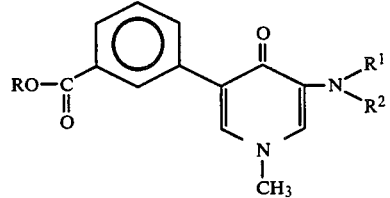

(I)

| Example No. | R | $-N\begin{matrix}R^1\\R^2\end{matrix}$ | Melting point (°C.) |
|---|---|---|---|
| 6 | $C_2H_5$ | -N-N (pyrazolyl) | 144 |
| 7 | $(CH_3)_2CH-$ | -N-N (pyrazolyl) | 122 |
| 8 | $CH_3-(CH_2)_3-$ | -N-N (pyrazolyl) | 96–98 |
| 9 | $(CH_3)_3C-$ | -N-N (pyrazolyl) | 75 |
| 10 | $(CH_3)_2CH-CH_2-$ | -N-N (pyrazolyl) | 118–120 |
| 11 | $(C_2H_5)_2CH-CH_2-$ | -N-N (pyrazolyl) | 95–98 |
| 12 | $ClCH_2CH_2-$ | -N-N (pyrazolyl) | 134–135 |
| 13 | $CH_3(CH_2)_2\overset{CH_3}{\underset{|}{C}H}-CH_2-$ | -N-N (pyrazolyl) | 63–65 |
| 14 | benzyl-$CH_2-$ | -N-N (pyrazolyl) | 102–105 |
| 15 | cyclohexyl (H) | -N-N (pyrazolyl) | 118–120 |

TABLE 2-continued (I)

$$\text{RO-C(=O)-[phenyl]-[pyridinone with N-CH}_3\text{, 4-oxo, 5-NR}^1\text{R}^2\text{]}$$

| Example No. | R | $-N\langle{}^{R^1}_{R^2}$ | Melting point (°C.) |
|---|---|---|---|
| 16 | HC≡C—CH$_2$— | —N(pyrazolyl) | 110–112 |
| 17 | (CH$_3$)$_3$C—CH$_2$— | —N(pyrazolyl) | 122–123 |
| 18 | (CH$_3$)$_2$CH—CH$_2$CH(CH$_3$)— | —N(pyrazolyl) | $n_D^{35}$ = 1.5929 |
| 19 | CH$_2$=CH—CH$_2$— | —N(pyrazolyl) | 75 |
| 20 | CH$_3$O—CH$_2$CH$_2$— | —N(pyrazolyl) | 96 |
| 21 | CH$_3$—(CH$_2$)$_2$NH$_3^\oplus$ | —N(pyrazolyl) | 105–108 |
| 22 | [(CH$_3$)$_2$CH—CH$_2$]$_2$NH$_2^\oplus$ | —N(pyrazolyl) | 80–81 |
| 23 | [CH$_3$(CH$_2$)$_2$]$_2$NH$_2^\oplus$ | —N(pyrazolyl) | 120–122 |
| 24 | (C$_2$H$_5$)$_3$NH$^\oplus$ | —N(pyrazolyl) | crystal sludge |
| 25 | (CH$_3$)$_2$NH$_2^\oplus$ | —N(pyrazolyl) | 118–120 |
| 26 | [CH$_3$(CH$_2$)$_3$CH(C$_2$H$_5$)—CH$_2$—]$_2$NH$_2^\oplus$ | —N(pyrazolyl) | crystal sludge |

TABLE 2-continued
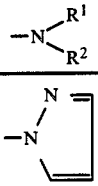
(I)
| Example No. | R | $-N\begin{matrix}R^1\\R^2\end{matrix}$ | Melting point (°C.) |
|---|---|---|---|
| 27 | $(C_2H_5)_2\overset{\oplus}{N}H_2$ | 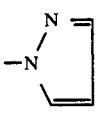 | 93 |
| 28 | $[CH_3(CH_2)_3-]_2\overset{\oplus}{N}H_2$ |  | 150–153 |
| 29 | $CH_3(CH_2)_3\underset{C_2H_5}{CH}CH_2-$ | 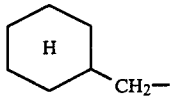 | 90–91 |
| 30 | 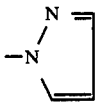 | 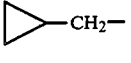 | 158–160° C. |
| 31 |  | 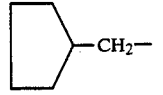 | 126 |
| 32 |  |  | |
| 33 | Na⊕ |  | 155 |
| 34 | ½Ba²⊕ |  | >320 |
| 35 | CH₃ |  | 158–160 |
| 36 | CH₃ | 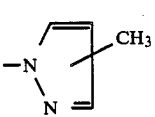 | Oil |
| 37 | $(CH_3)_2CH-CH_2-CH_2-$ | | Oil |

TABLE 2-continued (I)

[Structure: 3-(RO-C(=O))-phenyl substituted 1-methyl-4-oxo-1,4-dihydropyridine with -NR¹R² group]

| Example No. | R | -NR¹R² | Melting point (°C.) |
|---|---|---|---|
| 38 | $(CH_3)_2CH-CH_2-CH_2-$ | 1-imidazolyl | Oil |
| 39 | $(C_2H_5)_2CH-CH_2-$ | 1-imidazolyl | Oil |
| 40 | $(CH_3)_2CH-CH_2-CH_2-$ | 1-(1,2,4-triazolyl) | 160–161 |
| 41 | $(C_2H_5)_2CH-CH_2-$ | 1-(1,2,4-triazolyl) | 105 |
| 42 | $CH_3-(CH_2)_3-$ | 1-(1,2,4-triazolyl) | 166 |
| 43 | $(CH_3)_2CH-CH_2-CH_2-$ | 3,5-dimethyl-1-pyrazolyl | Oil |
| 44 | $CH_3-(CH_2)_3-$ | 3,5-dimethyl-1-pyrazolyl | Oil |
| 45 | $(C_2H_5)_2CH-CH_2-$ | 3,5-dimethyl-1-pyrazolyl | Oil |

USE EXAMPLES

The compound shown below was employed as the comparison substance in the following use example:

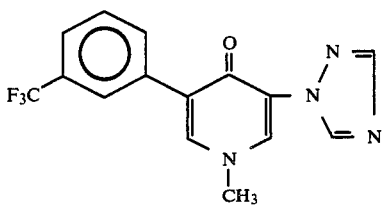

(A)

1-Methyl-3-(1,2,4-triazol-1-yl)-5-(3-trifluoromethyl-phenyl)-4-pyridone (known from European Published Application A2-0,073,999 and U.S. Pat. No. 4,451,282).

EXAMPLE A

Pre-emergence test

Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a clearly superior activity, with a comparable selectivity for useful plants, to the prior art is shown, for example by the compound according to the following preparation example: 11.

It is understood that the specification and examples are illustrative but not limitative of the present invention and that other embodiments within the spirit and scope of the invention will suggest themselves to those skilled in the art.

We claim:

1. An N-methyl-4-pyridone in which

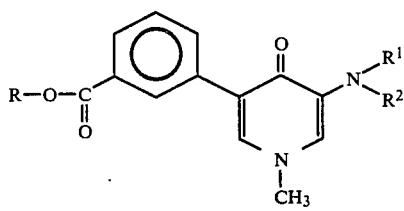

R represents hydrogen, or represents alkyl, alkenyl or alkynyl, each of which is straight-chain or branched and has up to 18 carbon atoms, or represents straight-chain or branched alkoxy-alkyl with in each case up to 12 carbon atoms in the individual alkyl parts, or represents straight-chain or branched halogenoalkyl with up to 3 carbon atoms, or represents cycloalkyl with 3 to 7 carbon atoms, or represents straight-chain or branched aralkyl which has up to 4 carbon atoms in the alkyl part and 6 to 10 carbon atoms in the aryl part and which may be substituted in the aryl part by at least one member selected from the group consisting of halogen, cyano, nitro and alkyl, alkoxy or halogenoalkyl each of which is straight-chain or branched and has up to 4 carbon atoms and is optionally halogen-substituted, or represents one equivalent of an alkali metal or alkaline earth metal cation, or represents an ammonium ion of the formula

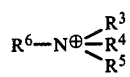

wherein
$R^3$, $R^4$, $R^5$ and $R^6$ independently of one another in each case represent hydrogen, or represents straight-chain or branched alkyl with up to 18 carbon atoms, or represent cycloalkyl with 3 to 7 carbon atoms, or represent straight-chain or branched aralkyl with up to 4 carbon atoms in the alkyl part and 6 to 10 carbon atoms in the aryl part, and
$R^1$ and $R^2$, together with the nitrogen atom to which they are bonded, represent 1,2,4-triazol-1yl, imidazol-1-yl or pyrazol-1-yl which may be substituted by alkyl or alkoxy with in each case up to 4 carbon atoms or halogen.

2. An N-methyl-4-pyridone according to claim 1, in which
R represents hydrogen, methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, allyl, butenyl, pentenyl, hexenyl, propargyl, butynyl, pentynyl, hexynyl, methoxymethyl, methoxyethyl, ethoxyethyl, isopropoxyethyl, methoxypropyl, chloromethyl, dichloromethyl, trichloromethyl, trifluoromethyl, 2-chloroethyl, 2,2,2-trichloroethyl, 2-bromoethyl, 2,2,2-tribromoethyl, 3-chloropropyl, cyclopropyl, cyclopentyl, cyclohexyl or cycloheptyl, or represents benzyl or phenethyl, each of which is optionally mono-, di- or tri-substituted by identical or different substituents from the group consisting of fluorine, chlorine, bromine, methyl, ethyl, methoxy, ethoxy, cyano and trifluoromethyl, or represents one equivalent of a sodium, potassium, calcium, magnesium or barium ion or ammonium ion of the formula

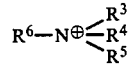

wherein
$R^3$, $R^4$, $R^5$ and $R^6$ independently of one another each represent hydrogen, methyl, ethyl, n- or i-propyl, n-, i-, s- or t-butyl, n- or i-pentyl, n- or i-hexyl, n- or i-heptyl, n- or i-octyl, cyclopentyl, cyclohexyl or benzyl and
$R^1$ and $R^2$, together with the nitrogen atom to which they are bonded, represent 1,2,4-triazol-1-yl, imidazol-1-yl or pyrazol-1-yl each of which is optionally substituted by methyl, methoxy and/or chlorine.

3. A compound according to claim 2, wherein such compound is 5-[3-(3-methylbutoxycarbonyl)-phenyl]-1-methyl-3-(pyrazol-1-yl)-4-pyridone of the formula

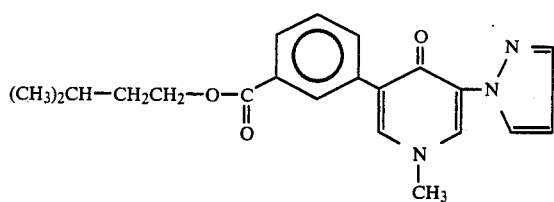

4. A compound according to claim 2, wherein such compound is 5-(3-n-butoxycarbonyl-phenyl)-1-methyl-3-(pyrazol-1-yl)-4-pyridone of the formula

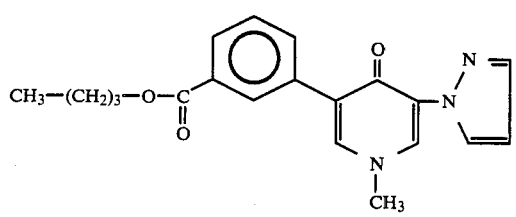

5. A compound according to claim 1 wherein such compound is 5-[3-(1,3-dimethylbutoxycarbonyl)-phenyl]-1-methyl-3-(pyrazol-1-yl)-4-pyridone of the formula

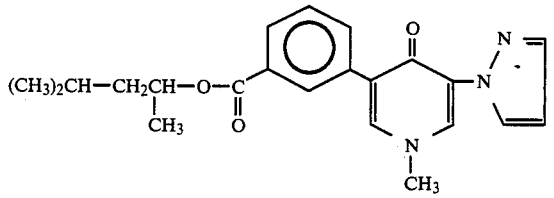

6. A compound according to claim 1, wherein such compound is 5-[3-(2-methoxyethoxycarbonyl)-phenyl]-1-methyl-3-(pyrazol-1-yl)-4-pyridone of the formula

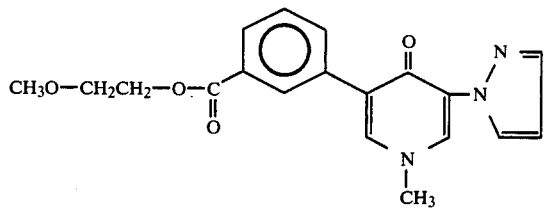

7. A compound according to claim 1, wherein such compound is 5-(3-cyclohexylmethoxycarbonyl-phenyl)-1-methyl-3-(pyrazol-1-yl)-pyridone of the formula

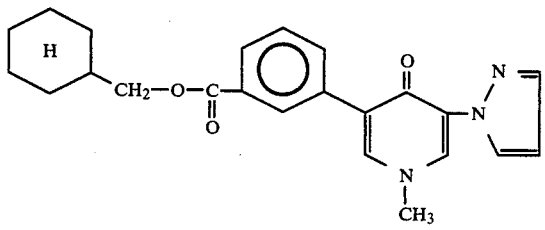

8. A herbicidal composition comprising a herbicidally effective amount of a compound according to claim 1 in admixture with a diluent.

9. A method of combating unwanted vegetation which comprises applying to such vegetation or to a locus from which it is desired to exclude such vegetation a herbicidally effective amount of a compound according to claim 1.

10. The method according to claim 9, wherein such compound is
5-[3-(3-methylbutoxycarbonyl)-phenyl]-1-methyl-3-(pyrazol-1-yl)-4-pyridone,
5-(3-n-butoxycarbonyl-phenyl)-1-methyl-3-(pyrazol-1-yl)-4-pyridone,
5-[3-(1,3-dimethylbutoxycarbonyl)-phenyl]-1-methyl-3-(pyrazol-1-yl)-4-pyridone,
5-[3-(2-methoxyethoxycarbonyl)-phenyl]-1-methyl-3-(pyrazol-1-yl)-4-pyridone or
5-(3-cyclohexylmethoxycarbonyl-phenyl)-1-methyl-3-(pyrazol-1-yl)-pyridone.

* * * * *